US00PP10254P

United States Patent [19]

van Andel

[11] Patent Number: Plant 10,254

[45] Date of Patent: Feb. 24, 1998

[54] ALSTROEMERIA PLANT VARIETY NAMED 'STABELIN'

[75] Inventor: Jacob van Andel, Aalsmeer, Netherlands

[73] Assignee: Van Staaveren b.v., Aalsmeer, Netherlands

[21] Appl. No.: 728,154

[22] Filed: Oct. 9, 1996

[51] Int. Cl.[6] ..... A01H 5/00

[52] U.S. Cl. ..... Plt./87.1

[58] Field of Search ..... Plt./87.1

*Primary Examiner*—James R. Feyrer
*Assistant Examiner*—Elizabeth C. Kemmerer
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 87R1280-1 and as pollen parent an unreleased, unpatented seedling identified as 87G1069-02 from among my collection of Alstroemeria seedlings maintained under controlled conditions in a greenhouse at Van Staaveren B.V., Aalsmeer, The Netherlands, for developmental purposes. The varietal denomination of the new variety is 'Stabelin'.

The first act of asexual reproduction of 'Stabelin' was in Aalsmeer, The Netherlands, by propagation by dividing rootstocks. Asexual reproduction by dividing rootstocks in Aalsmeer, The Netherlands, through successive generations has demonstrated that the combination of characteristics as herein disclosed for 'Stabelin' are firmly fixed and retained through successive generations of asexual reproduction.

SUMMARY OF THE INVENTION

The new variety of Alstroemeria, 'Stabelin' is characterized by flowers of unusual coloration, as described herein.

DESCRIPTION OF ILLUSTRATIONS

The new variety of Alstroemeria hybrid is illustrated in the accompanying illustration, which shows typical growth and flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations. 'Stabelin' has not been observed under all possible environmental conditions. Phenotypic expression may vary with variations in environment such as temperature, light intensity, day length and growing and cultural conditions.

Botanical classification:
- *Family.*—amaryllidaceae Genus: Alstroemeria sp. Commercial: Alstroemeria hybrid.

Origin: Seedling.

Plant

Form: Bush.
Shape: Upright.
Height: About 175 to 225 cm.
Main stem or cane length: About 200 cm.
Growth: Vigorous, medium growth rate.
Strength: Strong.
Foliage:
- *Quantity.*—Abundant.
- *Number of leaves.*—About 25 to 30.
- *Size of leaf.*—Length: About 16 to 22 cm. Width: About 3 to 4 cm.
- *Shape of leaf.*—Elliptical.
- *Margin type.*—Straight.
- *Texture.*—Glossy.
- *Color.*—Upper side: Near 137A. Underside: Near 137B.
- *Rhizomes.*—Yes. Color: Near 155D. Size: About 10–30 cm.

Inflorescence—Flower Floret

Blooming habit: Recurrent.
Blooms: Profusely.
- *Spring.*—Yes.
- *Fall.*—Yes.
- *Has tendency to give few blooms in fall.*—No.

Size: Medium.
- *Diameter.*—About 6 cm.
- *Depth.*—About 5 cm.

Borne: Singly.
Shape or form:
- *When bloom first opens.*—Cup.
- *When bloom matures.*—Cup.

Petalage:
- *Number of petals.*—6.
- *Arrangement.*—Two concentric circles of 3 petals.
- *Form.*—Obovate.
- *Margin type.*—Straight.
- *Apex.*—Pointed.
- *How long do petals stay on stem?*—About 3 weeks.
- *Texture.*—Soft.
- *Appearance.*—Velvety.
- *Color.*—Outer petal/floret: Body near 10C; base near 10C; reverse side near 10C; 0 to 1 stripes, near 187A. Inside lateral petal: Body near 14A/10C; base near 10C; reverse side near 14A/10C; about 30 to 40 stripes, near 187A. Inside median petal: Body near 10C; base near 10C; reverse side near 10C; about 30 to 40 stripes, near 187A.

Peduncle or flower stem:

*Length.*—About 10 to 15 cm.

*Color.*—Near 137B to 137C.

*Strength.*—Strong.

*Upright.*—Yes.

Discoloration after full bloom?: Slightly.

Is bloom affected by wet or hot weather?: No.

Persistence (does flower hang on and dry?): No.

Disease resistance: Unknown.

Fragrance: None.

Lasting quality:

*On plant.*—About 3 weeks.

*As cut flower.*—About 14 days.

Bud

Size:

*Diameter.*—About 1 to 2 cm.

*Depth or length.*—About 2 to 3 cm.

Form or shape: Pear-shaped.

*Long.*—About 2 to 3 cm.

*Pointed.*—No.

Rate of opening: Fast.

Color of petals/florets:

*When petals begin to unfurl.*—Near 10C.

*When sepals/phyllaries first divide.13* Near 10C.

Peduncle or flower stem:

*Length.*—About 10 to 15 cm.

*Hairy.*—No.

*Strength or character.*—Erect.

*Color.*—Near 137B to 137C.

*Sepals.*—No.

*Calyx.*—No.

Reproductive Organs

Stamen:

*Number.*—6.

*Arrangement.*—Around the style.

Anthers:

*Size.*—About 6 to 8 mm.

*Color.*—Near 11A.

Filaments:

*Length.*—About 4 to 5 cm.

*Color.*—Near 8B.

Pollen:

*Color.*—Near 13A.

Pistils:

*Number.*—1.

Styles:

*Length.*—About 4 to 5 cm.

*Color.*—Near 8B.

Stigmas:

*Color.*—Near 8B.

Fruit

Fertile: Yes.

Shape: Round.

Color at maturity: Near 163A.

I claim:

1. A new plant variety of Alstroemeria plant substantially as herein shown and described.

* * * * *

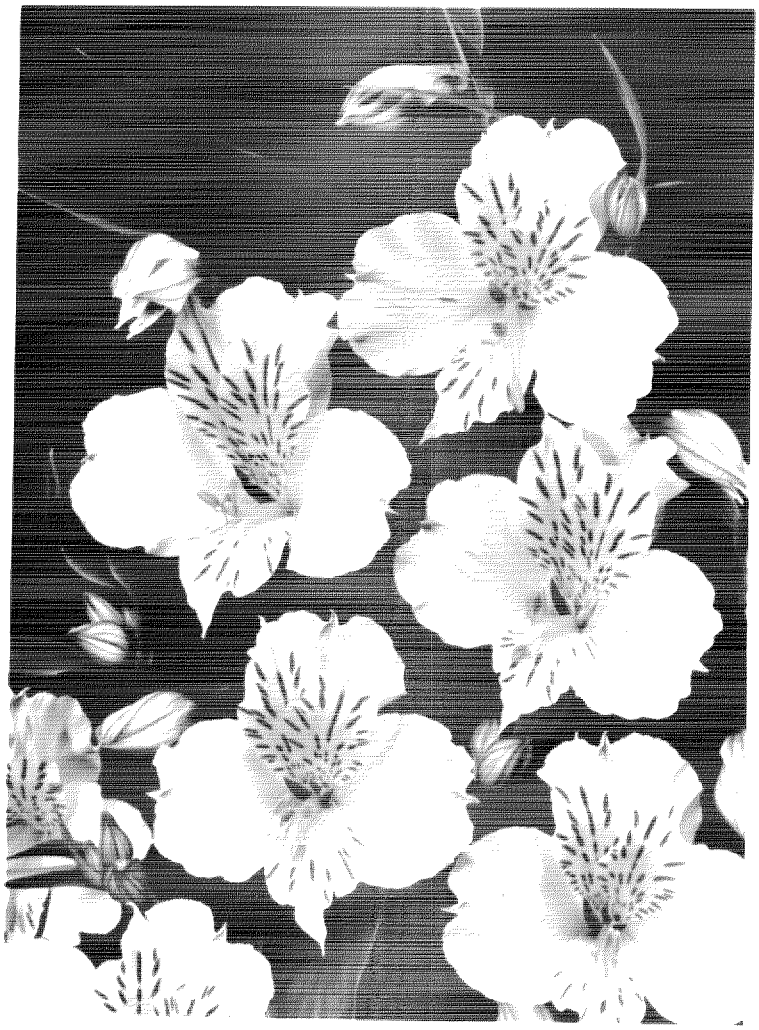

UNITED STATES PATENT AND TRADEMARK OFFICE

CERTIFICATE OF CORRECTION

PATENT NO. : Plant 10,254
DATED : February 24, 1998
INVENTOR(S) : Jacob van Andel It is certified that error appears in the above-identified patent and that said Letters Patent is hereby corrected as shown below:

Column 3, line 26, after "*first divide.*" delete "13".

Signed and Sealed this

Second Day of February, 1999

*Attest:*

*Attesting Officer*

*Acting Commissioner of Patents and Trademarks*